United States Patent [19]
Gosset et al.

[11] Patent Number: 6,037,311
[45] Date of Patent: Mar. 14, 2000

[54] PHYTOSANITARY COMPOSITION, METHOD OF PREPARING SAME AND USE THEREOF, ESPECIALLY COMBATTING WEEDS

[75] Inventors: Serge Gosset, Lestrem; Christian Gauvrit, Dijon, both of France

[73] Assignee: Roquette Freres, France

[21] Appl. No.: 08/339,645

[22] Filed: Sep. 26, 1996

Related U.S. Application Data

[63] Continuation of application No. 07/971,984, filed as application No. PCT/FR92/00520, Jun. 10, 1992, abandoned.

[30] Foreign Application Priority Data

Jun. 10, 1991 [FR] France .................. 91 07012

[51] Int. Cl.⁷ .................................. A01N 43/80
[52] U.S. Cl. ................ 504/138; 504/140; 504/116; 504/292; 504/322; 504/149
[58] Field of Search .................... 504/271, 116, 504/138, 140, 292, 322, 149

[56] References Cited

FOREIGN PATENT DOCUMENTS 049071  4/1982  European Pat. Off. .

OTHER PUBLICATIONS

Derwent Abstract, No. 137240/20, Jul. 13., 1988, Week 8820 (Corresponding to JP 63 079 802, Apr. 9, 1988).

*Primary Examiner*—Brian M. Burn
*Assistant Examiner*—B. Bembenick
*Attorney, Agent, or Firm*—Blakely Sokoloff Taylor & Zafman

[57] ABSTRACT

Phytosanitary composition for use especially in affording protection to plants from undesirable plant species. The composition is characterized in that it contains at least one benzamidic compound associated with at least one cyclodextrine to improve mobility in the ground and/or the biological afficacy of the benzamidic derivative. The invention also concerns a method of preparing the phytosanitary composition.

18 Claims, 1 Drawing Sheet

PHYTOSANITARY COMPOSITION, METHOD OF PREPARING SAME AND USE THEREOF, ESPECIALLY COMBATTING WEEDS

This is a continuation of application Ser. No. 07/971,984 filed Feb. 10, 1993 (Abandoned), which is a National Stage Application filed under 35 U.S.C. 371 of PCT/FR92/00520 filed Jun. 10, 1992.

The present invention relates to, as new industrial products, plant protection compositions based on benzamide compound(s) and cyclodextrin(s), which are useful especially for protecting plants against undesirable plant species.

Another subject of the invention is a process for the preparation of the said compositions and their use in post- and/or preemergence of the plants to be protected.

Finally, the present invention relates, very particularly, to the preparation of plant protection compositions containing, as benzamide compound possessing a herbicidal activity, N-[3-(1-ethyl-1-methylpropyl)-5-isoxazolyl]-2,6-dimethoxybenzamide, also known under the name "Isoxaben", and to their use for the purpose of protecting crops, especially cereal crops.

"Plants" means especially any plant species cultivated by man, in particular those intended for feeding man or animals (cereals, fodder crops, vegetable crops, fruit crops, vines, and the like), and/or for supplying wood for all purposes (heating, house construction, furniture making, and the like) and/or for ornamentation (silviculture, ornamental, floral, turf, and similar cultivations).

"Undesirable plant species" means those which act unfavourably on the targeted use(s) of cultivated plants and, in particular, those whose presence qualitatively and/or quantitatively harms the growth and/or the harvesting of all or part of the cultivated plants.

This definition includes all the plant species described, in everyday speech, as "weeds", especially those belonging to the dicotyledon class.

It has already been recommended, in an article by Szejtli, to treat seeds of cultivated plants, in particular by steeping, with solutions of linear dextrins and/or of cyclic dextrins (cyclodextrins) for the purpose of delaying germination of the said seeds.

The growth of the shoots would thus be stimulated and the plants would prove to be less sensitive to the phytotoxicity of herbicides used subsequently ("Physiological Effects of Cyclodextrins in Plants"—die Starke, 35 (1983), No. 12, pp. 443–438).

It is said in this article that this "antidote" effect can make it possible to lower the sensitivity of cultivated plants to certain herbicides ("Dicuran", "Afalon" and "Hungazin") but does not influence the effectiveness of the said herbicides against weeds.

Moreover, in the Belgian Patent BE No. 902,613, the preparation and the use of complexes based on beta-cyclodextrin and on specific derivatives of benzenesulphonylurea possessing herbicidal activity was described.

It appears that the claimed complexes, which are presented as improving the biological effectiveness of the benzenesulphonylureas, require the obligatory use of at least two moles of beta-cyclodextrin per mole of active principle.

It is appropriate to recall, at this point of the description, that one of the necessary conditions for a herbicidal active principle to be truly effective resides in the ability of the said active principle to affect in sufficient quantities, inside the soil, the weeds and/or the seeds of each of the undesirable plant species for which it is intended.

Certain compounds possessing herbicidal activity therefore see their potential or effective applications reduced because they are supposed to be or are recognised to be, in certain circumstances, ineffective, especially through lack of a sufficient mobility in the substrate intended to support the plant to be protected.

This mobility is very obviously influenced by the intrinsic chemical nature of the herbicide but also by external factors connected, inter alia, to the physicochemical nature and to the dampness of the substrate.

Jamet et al. have, for example, shown that herbicides such as the products known under the respective names of "Metamitron" and "Atrazine" have a different mobility, expressed according to the classification in five classes of Helling and Turner, depending on the nature of the soil to which they had been applied (Bull. Environ. Contam. Toxicol. (1988), 41: 135–142).

In this document, Atrazine is classed, by way of example, as "immobile" (class 1) in certain substrates and "slightly mobile" (class 2) or "moderately mobile" (class 3) in certain others.

In this same document, Jamet showed that a benzamide herbicide such as N-[3-(1-ethyl-1-methylpropyl)-5-isoxazolyl]-2,6-dimethoxybenzamide, also known under the name "Isoxaben", could be considered as perfectly immobile (class 1) independently of the nature of the substrate to which it had been applied.

Isoxaben is more particularly used as a preemergence herbicide in the context of protecting winter cereals such as soft wheat, hard wheat, barley, oats, triticale or rye.

It is generally applied, in autumn, by spraying on the soil (mean dose: 125 g/hectare) and, in this context, benefits from the rains up to spring which ensures its slow distribution in the surface layer of the soil where the majority of the weeds to be removed, especially the dicotyledons, germinate. It can also enter into the seed during the inhibition phase which preceeds germination.

Now, although this product regularly shows a real biological effectiveness in the context of protecting winter wheat, for example, it is not the same when it comes to treating crops which, like maize, require weed control during the month of May.

Indeed, during this period, rainfall is very irregular from one year to another and, in general, is low in comparison with winter precipitation.

Environmental conditions, in particular in the soil, are consequently often too dry for Isoxaben to have a good herbicidal effectiveness and especially a sufficient mobility to enable it to significantly affect and destroy undesirable plant species.

It is clear that what has just been said on the subject of Isoxaben is capable of being applied to any benzamide compound possessing herbicidal activity whose mobility and/or effectiveness is potentially or effectively insufficient in such a context, especially those which can be described as "immobile" or "slightly mobile" in the substrate(s) intended to support the targeted crops.

Consequently, such active principles, in particular Isoxaben, see their uses limited as regards their application to the protection of cultivated plants whose weed control takes place from May to the end of summer (maize, for example) or under exceptional conditions of low rainfall in autumn/winter.

It emerges from the above, that it was necessary to find a means capable of making possible a wider use of these products, in particular in their use as preemergence herbicides applied to soil surfaces.

The success of the Applicant Company lies in having found that such a means could consist in combining, in the presence or absence of third constituents, at least one of these products, namely a benzamide compound, and at least one cyclodextrin, in particular a beta-cyclodextrin.

More precisely, the subject of the present invention is a plant protection composition, useful especially for protecting plants against undesirable plant species, characterised in that it contains at least one benzamide compound in combination with at least one cyclodextrin so as to improve the mobility in the soil and/or the biological effectiveness of the said benzamide derivative.

The present invention assumes an especially surprising and unexpected nature since investigations specifically targeting the screen simulation, by computer-aided modelling, of molecular systems between cyclodextrins and various active principles have shown that Isoxaben and beta-cyclodextrin could not be the subject of true inclusion complexes, in contrast to other active principles studied (Minutes, 5th Int. Symposium on Cyclodextrins, Mar. 28–30 1990, p. 101–106).

Well aware of this teaching, the specialist in the formulation of plant protection compositions containing benzamide compounds had no inclination to wish to study the incorporation of cyclodextrins, in particular of beta-cyclodextrin, in these compositions, especially since the latter generally contain, as will be explained in more detail subsequently, other constituents capable of interacting, in one way or another, with the said cyclodextrins and of disturbing the biological effectiveness of the whole.

In addition, the success of the Applicant Company lies in having found, after long studies, that not only the combination of a cyclodextrin and a benzamide herbicide, including the presence of third constituents, was of real importance in plant protection application, but also that this importance manifested itself most advantageously for cyclodextrin/benzamide compound molar ratios which were low and, in particular, significantly lower than those made obligatory according to the above-mentioned Patent BE 902,613.

In the context of the present invention, benzamide compound means any compound capable of having, among other functional groups, a herbicide functional group which corresponds to the general formula below:

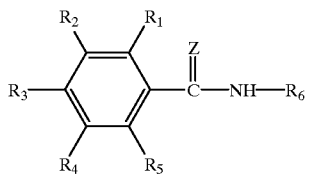

in which Z is an oxygen or sulphur atom.

The groups $R_1$ to $R_6$, which can be identical or different, are especially of hydrogen, halogen, alkyl, including hydroxy-, halo- or thioalkyl, alkenyl, alkoxy, especially methoxy or ethoxy, or aryl type.

In particular, the term "aryl" is in no way limiting, especially in its application to the group $R_6$ and the general formula given above must be understood as including, inter alia, the N-arylbenzamide compounds described in the Patent EP-A-0,049,071, in particular from line 17 of page 1 to line 55 of page 12, this passage being incorporated in the present description.

This definition applies, by way of example, to the above-mentioned N-arylbenzamide compounds whose group $R_6$ is thus of "aryl" type and at least one of whose groups $R_1$ to $R_5$ is of alkoxy type, preferably of methoxy or ethoxy type.

In the context of the invention, in this category of N-aryl (alkoxy)benzamide compounds, reference will be made in particular to the products described from line 5, page 11 to line 45, page 12 of the abovementioned Patent EP-A-0,049, 071, and especially Isoxaben, and to their salts which are acceptable in agronomy.

The term "cyclodextrin" means any macrocycle constructed from six, seven or eight glucose units and denoted respectively by alpha-, beta- or gamma-cyclodextrin, as well as any derivative whatsoever of these. The term "derivative" must be understood as comprising any macrocycle such as defined above, at least one of whose constituent glucose units is substituted, at least in one place, by a group or a molecule which can be very varied in size and functionality, such as, for example, an alkyl group and especially hydroxyalkyl, such as a hydroxypropyl group, or, for example, a mono- or disaccharide molecule, such as a molecule of maltose, glucose, fructose or sucrose.

In the context of the invention, a cyclodextrin chosen from the group comprising beta-cyclodextrin and its derivatives, alpha-cyclodextrin and its derivatives, as well as any mixtures whatsoever of at least any two of these products is preferably used.

The said mixtures can, by way of example, contain jointly, and in variable proportions, each of the three types of abovementioned cyclodextrins (alpha, beta and gamma) as well as, optionally, other constituents such as linear dextrins and/or other more or less complex saccharide structures.

Entirely advantageously, the cyclodextrin characteristically used in the compositions according to the invention consists essentially of beta-cyclodextrin and/or of one of its derivatives, in particular hydroxyalkylated.

As stated above, the plant protection compositions according to the invention have, surprisingly, a maximum effectiveness at low cyclodextrin(s)/benzamide compound (s) molar ratios.

According to a preferential embodiment of the invention, this molar ratio is no more than approximately 2/1 and is more particularly between 0.1/1 and 1/1.

These compositions could exist in very varied solid or liquid forms and, for example, in the form of wettable powders, concentrated suspensions, slurries, aerosols, powders for dusting or dispersion, solutions, water-soluble concentrates, emulsifiable concentrates, emulsions, and the like.

The characteristic presence of at least one cyclodextrin in these compositions does not in any way prevent the latter from being able to be treated with products generally used in formulation such as, especially, vehicles, diluting agents or solvents, surfactants, dispersing agents, emulsifying agents, antifreezes and dyes.

The adjuvants described from line 26, page 65 to line 62, page 65 of the abovementioned Patent EP-A-0,049,071 can be referred to.

The Applicant Company has additionally demonstrated the possibility of advantageously using xanthan gum as adjuvant, and especially as dispersing agent, in the said compositions.

Figure 1:
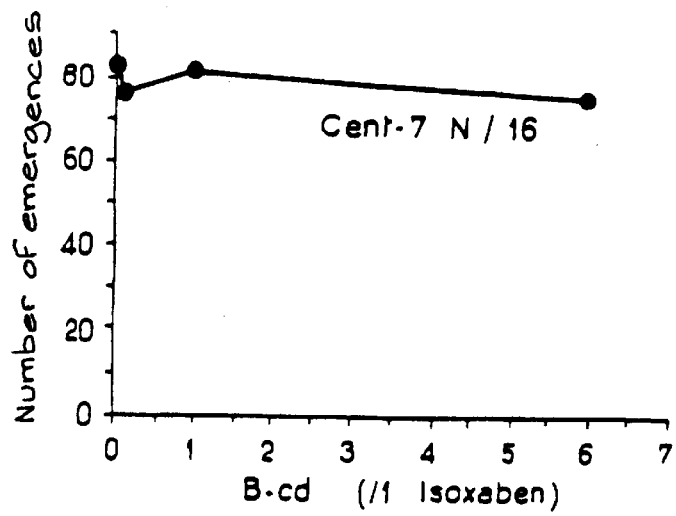
FIG. 1. The number of emergences of black nightshade according to the beta-cyclodextrin/Isoxaben ratio.

Likewise, the plant protection compositions according to the invention could contain, in addition to the benzamide compound(s), one or more other active materials, in particular possessing herbicidal, fungicidal, insecticidal, nematocidal or bactericidal activity.

In particular, the benzamide active material can be combined, in variable proportions, with one or more other herbicides of any nature other than benzamide, and especially chosen from the group comprising triazines, triazols, diazines, toluidines, urea derivatives, sulphonylureas, benzonitriles, amides, benzoic, phhalic (sic), picolinic or phenolic derivatives, and carbamates.

The herbicide which can be combined with the benzamide active material will preferably be chosen from the group comprising the products known under the names of Diuron, Methabenzthiazuron, Isoproturon, Linuron, Chlortoluron, Ametryn, Simazine, Trifluralin, Terbutryn, Propyzamide, Oxadiazon, Napropamide, Metazachlor, Alachlor and Prosulfocarb.

As regards the method of preparation of the compositions according to the invention, this stays simple and does not in any way require the availability of equipment and other technical means of implementation which are expensive and/or sensitive. However, particular attention will be paid to see that this preparation is carried out under conditions which ensure at best that intimate mixing between cyclodextrin(s) and benzamide compound(s) is obtained.

By way of example, it would be possible to prepare jointly, on the one hand, a solution of benzamide compound in a given solvent, for example a solution of Isoxaben in 30% ethanol and, on the other hand, a solution of cyclodextrin, for example of beta-cyclodextrin, in the same solvent and then to mix together the two solutions thus obtained.

Equally simply, it would be possible to use, in powder form, a cyclodextrin, especially beta-cyclodextrin, in a composition containing a preformulated herbicidal [lacuna] material which is already commercially available such as, for example, the formulation called "Cent-7" based on Isoxaben marketed by the Company Dow Elanco, as will be in another way exemplified elsewhere.

The commercial formulations to which cyclodextrin will be added could very obviously combine, in variable proportions, a benzamide compound, such as Isoxaben, and at least one other nonbenzamide herbicidal active material, such as those mentioned above.

These formulations could especially be those marketed by Dow Elanco under the names "Aubaine", "Ixo-7", "Sextan", "Crescendo", "Snapshot" or "Flexidor", by Ciba-Geigy under the names "Fanfare" or "Cibral" or by Bayer under the name "Glytex".

In consequence of which, a process for the preparation of a plant protection composition which is useful especially for protecting cultivated plants against undesirable plant species is henceforth available, characterised in that comprises a stage during which at least one benzamide compound possessing herbicidal activity and at least one cyclodextrin are brought together, in the presence or absence of third constituents, the cyclodextrin(s)/benzamide compound(s) molar ratio being preferably no more than approximately 2/1.

In any case, whatever the form of presentation and/or additive formulation of the plant protection compositions according to the invention, new industrial products are available which have undeniable advantages with respect to the traditional plant protection compositions using, as the only, or not the only, herbicidal active material, at least one benzamide compound, in particular a benzamide compound which can be classified as immobile or slightly mobile.

The compositions according to the invention make it possible, as will be exemplified below, to improve, in a surprising way, the effectiveness of the said benzamide compounds and, as a result, to make it possible, with respect to the compositions of the prior art, to undercharge these active materials without the effectiveness of the plant protection treatment being affected thereby.

By way of example, the preparation and the use, including for protecting cereals, of compositions which titrate less than approximately 125 g/l, especially from 5 to 120 g/l of active material and especially of Isoxaben can be envisaged.

On the one hand, the cyclodextrins result from renewable plant materials, namely amylaceous materials, and their biodegradability and their nontoxicity make them products which are perfectly tolerated by the environment.

In consequence of which, a new process for plant protection treatment, especially for the purpose of protecting cultivated plants against undesirable plant species is henceforth available, characterised by the use, in post- and/or preemergence of the plants to be protected, of a plant protection composition according to the invention, this composition preferably being applied to the surface of and/or inside the substrate intended to support or supporting the said plants.

If the use of the compositions according to the invention is most particularly essential for protecting cultivated plants which, like maize, require weed control between May and the end of summer, it is clear that these can generally be advantageously used to protect all the crops which, in a given period, must be freed of all or part of the weeds present, particularly those of the dicotyledon class, and especially must be applied to all the cereal crops (soft wheat, hard wheat, barley, oats, triticale, rye and winter barley), to vines and to ornamental trees and shrubs (conifers, for example).

Among the dicotyledon weeds capable of being efficiently destroyed by the use of the compositions according to the invention, there may be cited, without this list being limiting, the undesirable plant species belonging to the chenopodiaceae, amaranthaceae, cruciferae or solanaceae families.

It is possible entirely advantageously to use to this end, in particular in preemergence of the plants to be protected, compositions according to the invention which contain Isoxaben as benzamide compound, it being possible for the latter optionally to be combined with other herbicidal active materials.

The invention can be even better understood using the examples which follow and which take into account certain particularly advantageous embodiments of the compositions according to the invention.

The tests described below have the purpose of showing the importance of compositions according to the invention combining a cyclodextrin, especially beta-cyclodextrin marketed by the Applicant Company under the name Kleptose® B, and Isoxaben as benzamide compound, the latter being used as such or in the form of a composition containing preformulated herbicidal [lacuna] material (product "Cent-7" marketed by the Company Dow Elanco).

It is advisable to specify, as recalled above, that the use dose generally recommended for Isoxaben, at least for protecting cereals, is 125 g to the hectare (dose hereafter denoted dose N).

In the context of these tests, carried out on behalf of the Applicant Company at the Laboratoire de Malherbologie of the Institut National de la Recherche Agronomique (France), it was decided to use doses lower than dose N. Such doses do not completely destroy the treated weeds and must make it possible, by allowing an a priori mean herbicidal activity, to indicate possible profits or losses in the herbicidal effect more effectively.

Preliminary tests have thus made it possible to adopt the doses N/16 and N/8.

EXAMPLE 1

Preparations not in accordance with the invention, namely not characteristically containing cyclodextrin, were obtained by using, respectively, 125 and 250 microlitres of formulation Cent-7 in 1 litre of water.

The respective active material (Isoxaben) contents of these preparations, hereafter respectively denoted preparations T1 and T2, correspond respectively to the abovementioned doses N/16 and N/8.

Two compositions according to the invention, hereafter respectively denoted I1 and I2, were prepared in the same way except that 0.16 and 0.32 g/l, respectively, of Kleptose® B beta-cyclodextrin were used, jointly with the formulation Cent-7 in the proportions described above.

Consequently, the compositions according to the invention I1 and I2 are dosed respectively in Isoxaben at N/16 and N/8 and each have a cyclodextrin/benzamide compound molar ratio of 6/1.

Preparation of the Plant Material

In the context of this example, pregerminated amaranth (*Amaranthus albus*) and black nightshade (*Solanum nigrum*) seeds are used as undesirable plant species. It is appropriate to recall that black nightshade is a weed capable of colonising, inter alia, maize.

The seeds are pregerminated on petri dishes containing $10^{-4}$ m $GA_3$ gibberellic acid.

The black nightshade seeds are subjected, in an air conditioned enclosure, to an alternation of 16 h of light at 25° C. and 6 h of darkness at 20° C. until germination.

The amaranth seeds are placed for 16 h in light at 22° C. and 8 h in darkness at 14° C.

Protocols

Protocol A

Plastic pots are filled with 400 grams of a mixture of earth (2/3) and sand (1/3) sieved at 2 mm. They are adjusted to [lacuna] grams per 50% of field capacity (FC) and 480 grams per 100% of FC, this notion of field capacity or retention capacity corresponding to the maximum amount of water which the soil can retain under conditions where it can drain freely.

An experimental determination carried out on the soil used in the laboratory makes it possible to specify that the FCs of 100% correspond to a water content in the ground of 20%.

The preparations T1, T2, I1 and I2 are stirred for 30 minutes and the pots are then treated using a sprayer (pressure: 2 bar).

After treating, the seeds are planted at a ratio of 10 per pot. The test is placed in an air conditioned enclosure where temperature and humidity undergo the following cycle: 16 hours of light at 60% relative humidity and 22° C. and then 8 hours of darkness at 80% relative humidity and 14° C. The pots are daily brought back to 440 grams and 480 grams according to the desired field capacity degree using a nutritious solution containing, per litre:

10 ml of 40 g/l $KNO_3$ [sic] solution
13 ml of 72 g/l Ca $(NO_3)_2.4H_2O$ [sic]
15 ml of 25 g/l $MgSO_4.7H_2O$ [sic]
10 ml of 18.4 g/l $NaH_2PO_4.H_2O$ [sic]
1 ml of a solution containing:
1.86 g/l $H_3PO_3$ [sic]
1.69 g/l $MnSO_4.H_2O$ [sic]
0.25 g/l $CuSO_4.5H_2O$ [sic]
0.29 g/l $ZnSO_4.7H_2O$ [sic]
0.035 g/l $(NH_4)_6MO_7O_{24}.4H_2O$ [sic]
0.045 g/l $AlCl_3$ [sic]
0.025 g/l $COCl_3.H_2O$ [sic]
3.6 ml of a solution containing 0.557 g/100 ml of $FeSO_4.7H_2O$ and 0.745 g/100 ml of EDTA.

Evaluation of the results is made by harvesting, at the stage where the aerial part of the control plants (untreated) contain 2 true leaves, the aerial parts obtained for each treatment and then placing them in the oven at 80° C. for 24 hours. Weighing gives the weight of dry material thus recovered.

Protocol B

This protocol is used solely for black nightshade and in a soil wetted to 100% of its field capacity. The pots contain 30 black nightshades which have not undergone pregermination and are covered with a thin layer of earth.

The experiment comprises five repetitions.

The plants are harvested at the 4-true leaf stage of the control. The evaluation of the results is carried out in accordance with Protocol A. Additionally, the percentage of weed emergence obtained is noted.

Results

The results are expressed as a percentage of inhibition of the growth of the target weed, this percentage being determined by the formula below:

untreated control weight−test weight×100 untreated control weight the weights being those obtained after passing through the oven as described above.

Table I below shows the percentage of inhibition of growth obtained according to the target weed (amaranth, black nightshade), the herbicidal preparation tested (preparations T1 and T2 not in accordance with the invention, compositions I1 and I2 in accordance with the invention), the protocol used (Protocols A and B) and, for Protocol A, the field capacity tested (50 or 100%).

TABLE I

| Target Species | Protocol | Field Capacity | % Inhibition Herbicidal Preparation | | | |
|---|---|---|---|---|---|---|
| | | | I1 | I2 | T1 | T2 |
| Amaranth | A | 50* | — | — | — | — |
| | A | 100 | 19 | 48 | 44 | 83 |
| Black nightshade | A | 50 | 29 | 64 | 53 | 57 |
| | A | 100 | 73 | 65 | 73 | 78 |
| | B | 100** | 75 | 84 | 62 | 87 |
| | | | (10) | (10) | (6) | (5) |

*For this test, all the plants, including the untreated ones (control plants) showed difficulties in growing. The insignificant % of inhibition have not been shown.
**For this test, the figures in brackets show the % of emergence obtained.

Overall, it emerges from Table I that the compositions according to the invention I1 and I2 can be justifiably used as herbicidal compositions, especially when the benzamide compound is used in the form of a preformulated herbicidal [lacuna] material composition.

However, it appears that the tested compositions, which have a high cyclodextrin/benzamide compound molar ratio (6/1) do not make it possible, in all cases, to obtain results which are significantly different from those obtained in the control preparations T1 and T2 which have the same concentration of benzamide herbicide.

Additional tests carried out according to Protocol A (100% FC) on pregerminated amaranth seeds but using a beta-cyclodextrin derivative, in this case a hydroxypropylated beta-cyclodextrin prepared by the Applicant Company, as cyclodextrin used in the compositions according to the invention, have made it possible to arrive at the same general conclusions as above regarding the plant protection importance of the said compositions.

EXAMPLE 2

In the context of these tests, the effectiveness of plant protection compositions according to the invention which have low cyclodextrin/benzamide compound molar ratios, namely no more than the ratio 2/1 and especially between 1/1 and 0.125/1, is assessed on black nightshade (pregerminated seeds).

The cyclodextrin used in the compositions according to the invention is Kleptose® B beta-cyclodextrin marketed by the Applicant Company. The benzamide compound (Isoxaben) is used as such or introduced in the form of preparation Cent-7.

The retained dose of Isoxaben, for all the tested preparations (control preparations or preparations in accordance with the invention), is the N/16 dose defined above.

Preparation of the Plant Material

The tests take place in an airconditioned enclosure under an alternation 16 h of light (temperature 22° C., relative humidity 60%) and 8 h of darkness (14° C., 80%). The pots are daily brought back to the water content corresponding to the retention capacity of the field.

Preparation of the Compositions According to the Invention

Protocol A: use of Isoxaben as such

Solutions of Isoxaben in 96% ethanol (1.56 g/l) and beta-cyclodextrin in 30% ethanol (5.34 g/l) were mixed in 30% ethanol in proportions such that the cyclodextrin/benzamide compound molar ratios below are obtained: 2/1, 1/1, 0.5/1, 0.25/1 and 0.125/1.

10 ml of the final mixture diluted in 500 ml of water containing 0.1% xanthan gum and applied at a charge of 500 1/ha correspond to an N/16 dose of Isoxaben (7.8 g/ha).

Protocol B: use of Isoxaben in preformulated form

Preparations are obtained by using Cent-7 in water at a charge of 125 microlitres of Cent-7/1 and thus dosed in Isoxaben at N/16.

These preparations are made in accordance with the invention by using Kleptose® B beta-cyclodextrin for the purpose of obtaining the cyclodextrin/benazamide compound molar ratios of 6/1, 2/1, 1/1, 0.5/1, 0.25/1 and 0.125/1 respectively.

Growth Tests

For these tests, the pots are treated just before transplanting.

Black nightshade seeds are germinated on moist paper under an alternation 16 h of light (temperature 25° C.) and 8 h of darkness (20° C.). The germinated seeds are planted (3×10 per method) in pots filled with an earth/sand (2/1) mixture (sieved at 2 mm) adjusted in water to the retention capacity of the field. The earth comprises 32% clay and 2.3 organic matter. After treatment, the test is placed in the airconditioned enclosure. When the control plants reach the 2-true leaf stage, the aerial parts are harvested and placed in an oven at 80° C. for 24 h to determine the weight of dry matter.

Emergence Tests

For these tests, the pots are treated just after sowing.

3×100 black nightshade seeds are sown at a depth of 1 to 3 mm in the above-described mixture. After treatment, the test is placed in the airconditioned enclosure and the number of emerged plants is counted in the ten days which follow.

All the tests comprise 3 repetitions, a control and a reference Cent-7 at the same dose/ha as the Isoxaben contained in the preparations according to the invention.

Results

FIG. 1 appended shows the number of emergences obtained for the target weed (black nightshade) according to the beta-cyclodextrin/Isoxaben ratio of the herbicidal preparation tested.

As was described above, the preparations tested are dosed at N/16 in Isoxaben, the latter being introduced in the form of Cent-7 (cf. the above-described Protocol B).

The abscissa point 0 shows the number of emergences obtained for the control preparation Cent-7 which does not contain cyclodextrin.

It emerges from FIG. 1 that the compositions in accordance with the invention are, in terms of the number of weed emergences, at least as effective as the cyclodextrin-free preparation.

Figure 2:
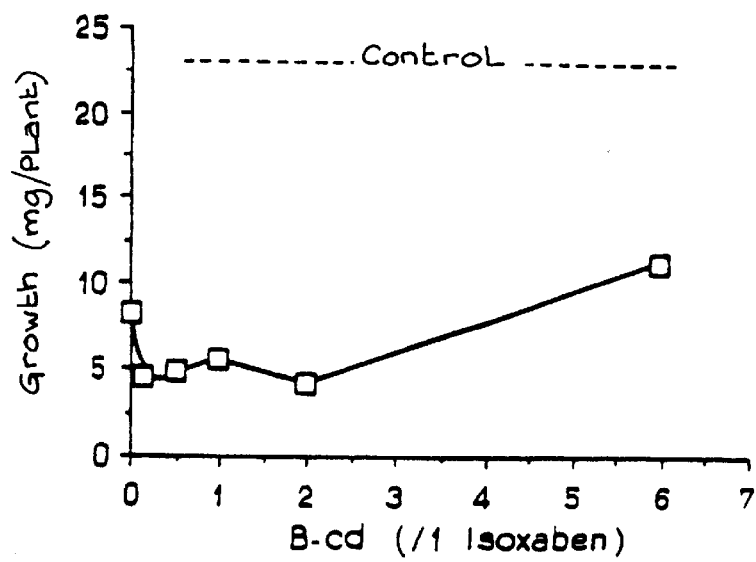
FIG. 2. Growth of black nightshade according to the beta-cyclodextrin/Isoxaben ratio.

FIG. 2 appended shows the growth of the target weed (black nightshade), expressed in mg/plant, according to the beta-cyclodextrin/Isoxaben ratio of the herbicidal preparation tested.

The tested preparations are dosed at N/16 in Isoxaben, the latter being introduced in the form of Cent-7 (compare Protocol B).

The abscissa point 0 shows the growth obtained for the control preparation Cent-7 which does not contain cyclodextrin.

A control test for which black nightshade is not subjected to any herbicidal treatment shows that, in this case, growth of black nightshade is approximately 23 mg/plant.

FIG. 2 confirms that all the tested compositions according to the invention can be justifiably used as plant protection herbicidal products.

Additionally, it emerges that, overall, the use of cyclodextrin, in particular beta-cyclodextrin, for cyclodextrin/benzamide compound ratios less than the approximately 2/1 molar ratio make it possible to achieve an effectiveness significantly greater than that of the cyclodextrin-free control preparation, in terms of inhibition of the mean growth of the target species.

Additional tests carried out with compositions according to the invention prepared according to the above-described Protocol A (Isoxaben introduced as such and not in preformulated form) have made it possible to draw the same conclusions as above, especially as regards the importance of compositions having a beta-cyclodextrin/benzamide compound molar ratio between approximately 0.125/1 and 1/1. By way of example, such compositions have made it possible to reduce the growth of the target weed (black nightshade) from approximately 2/3 to 4/5.

EXAMPLE 3

In the context of these tests, the effectiveness of the compositions according to the invention is tested on rape (*Brassica napus*) whose distinctive feature is to germinate relatively deeply with respect to black nightshade. Herbicides with low soil mobility would thus have even more difficulties in reaching it effectively. Additionally, this deep germination has the advantage of escaping possible light stimulus which can, in the context of low dosage, promote the emergence of the weed.

Preparation of the Plant Material

In the case of rape, the growth conditions are 16 h of light at a temperature of 19° C. and a humidity of 60% and 8 h of darkness at 9° C. and 80%.

The pots are daily brought back to the water content corresponding to the retention capacity of the field.

Preparation of the Compositions according to the Invention

It is carried out in accordance with Protocol A described in Example 2, for the purpose of obtaining compositions which have respective cyclodextrin/benzamide compound molar ratios of 2/1, 1/1, 0.5/1, 0.25/1 and 0.125/1, the said compositions being dosed at N/16 in Isoxaben.

In the present case, two control preparations using Isoxaben formulated in Cent-7 were tested for respective doses in active material of N/16 and N/20.

Emergence Tests

In the case of rape, the experimental conditions are identical to those described above for black nightshade, apart from the number of seeds sown (3×33), the earth/sand ratio (1/2) and the growth conditions (described above).

Results

Figure 3:
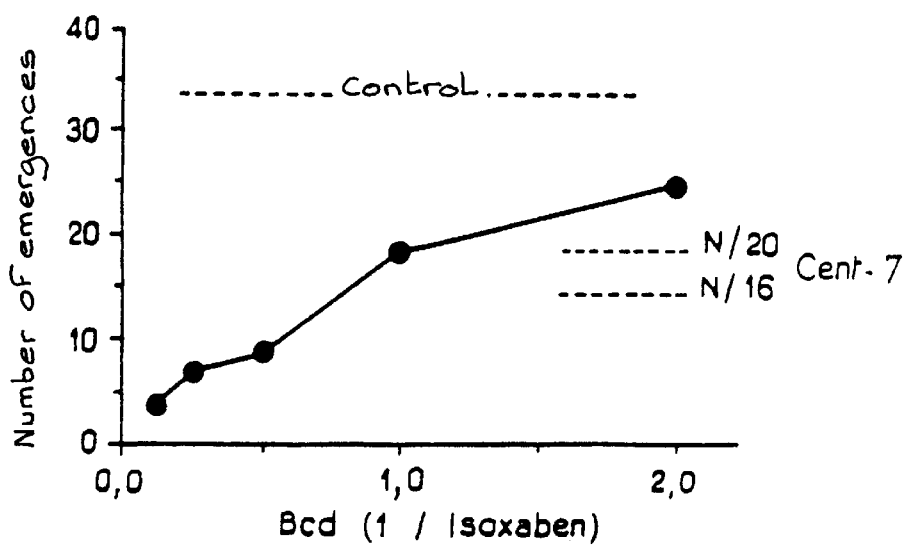
FIG. 3. The number of emergences of rape according to the beta-cyclodextrin/Isoxaben ratio.

FIG. 3 appended shows the number of emergences obtained for the target weed (rape) according to the beta-cyclodextrin/Isoxaben ratio of the herbicidal preparation tested.

It confirms, on a third target species, the importance of the compositions according to the invention which can, as in the present case, consist of simple formulations combining principally cyclodextrin, benzamide compound, water and dispersing agent (xanthan gum).

In particular, the compositions according to the invention having a cyclodextrin/benzamide compound ratio which is less than 2/1 and especially between approximately 1/1 and 0.125/1 are shown to be significantly more effective than an entirely formulated control herbicidal composition.

We claim:

1. Plant protection composition, useful for protecting plants against undesirable plant species, comprising at least one benzamide compound in combination with at least one cyclodextrin so as to improve the mobility of the benzamide compound in the soil, to increase the biological effectiveness of the benzamide compound or to improve both the mobility and increase the biological effectiveness of the benzamide compound, and the molar ratio of cyclodextrine(s), to benzamide compound(s) is no more than 2/1 and no less than 0.1/1.

2. Plant protection composition according to claim 1, characterized in that the molar ratio of cyclodextrin(s), to benzamide compound(s) is between 0.1/1 and 1/1.

3. Plant protection composition according to claim 1, characterized in that the benzamide compound is a N-arylbenzamide or a N-aryl alkoxybenzamide compound.

4. Plant protection composition, useful for protecting plants against undesirable plant species, comprising at least one benzamide compound in combination with at least one cyclodextrin so as to improve the mobility of the benzamide compound in the soil, to increase the biological effectiveness of the benzamide compound or to improve both the mobility and increase the biological effectiveness of the benzamide compound, and the molar ratio of cyclodextrine(s), to benzamide compound(s) is no more than 2/1 and no less than 0.1/1;

characterized in that the benzamide compound is an N-arylbenzamide or an N-aryl alkoxy benzamide compound; and further characterized in that the N-aryl alkoxybenzamide compound is N-[3-(1-ethyl-1-methylpropyl)-5-isoxazolyl]-2,6-dimethoxybenzamide (Isoxaben), or one of its salts.

5. Plant protection composition, useful for protecting plants against undesirable plant species, comprising at least one benzamide compound in combination with at least one cyclodextrin so as to improve the mobility of the benzamide compound in the soil, to increase the biological effectiveness of the benzamide compound or to improve both the mobility and increase the biological effectiveness of the benzamide compound, and the molar ratio of cyclodextrine(s), to benzamide compound(s) is no more than 2/1 and no less than 0.1/1;

characterized in that the benzamide compound is, as such, a product which is immobile or weakly mobile in the soil.

6. Plant protection composition, useful for protecting plants against undesirable plant species, comprising at least one benzamide compound in combination with at least one cyclodextrin so as to improve the mobility of the benzamide compound in the soil, to increase the biological effectiveness of the benzamide compound or to improve both the mobility and increase the biological effectiveness of the benzamide compound, and the molar ratio of cyclodextrine(s), to benzamide compound(s) is no more than 2/1 and no less than 0.1/1;

characterized in that the cyclodextrin is selected from the group consisting of beta-cyclodextrin and its derivatives, alpha-cyclodextrin and its derivatives, and mixtures thereof containing at least two of these products.

7. Plant protection composition, useful for protecting plants against undesirable plant species, comprising at least one benzamide compound in combination with at least one cyclodextrin so as to improve the mobility of the benzamide compound in the soil, to increase the biological effectiveness of the benzamide compound or to improve both the mobility and increase the biological effectiveness of the benzamide compound, and the molar ratio of cyclodextrine(s), to benzamide compound(s) is no more than 2/1 and no less than 0.1/1;

characterized in that the cyclodextrin is selected from the group consisting of beta-cyclodextrin and its derivatives, alpha-cyclodextrin and its derivatives, and mixtures thereof containing at least two of these products; and further characterized in that cyclodextrin consists essentially of beta-cyclodextrin and/or one of its derivatives.

8. Plant protection composition, useful for protecting plants against undesirable plant species, comprising at least one benzamide compound in combination with at least one cyclodextrin so as to improve the mobility of the benzamide compound in the soil, to increase the biological effectiveness of the benzamide compound or to improve both the mobility and increase the biological effectiveness of the benzamide compound, and the molar ratio of cyclodextrine(s), to benzamide compound(s) is no more than 2/1 and no less than 0.1/1;

characterized in that it additionally contains at least one adjuvant selected from the group consisting of vehicles, diluting agents, solvents, disbursing agents, surfactants, emulsifying agents, anti-freezes and dyes, and/or at least one additional active material selected from the group consisting of herbicides of non-benzamide nature, fungicides, insecticides, nematocides, and bactericides.

9. Plant protection composition, useful for protecting plants against undesirable plant species, comprising at least one benzamide compound in combination with at least one cyclodextrin so as to improve the mobility of the benzamide compound in the soil, to increase the biological effectiveness of the benzamide compound or to improve both the mobility and increase the biological effectiveness of the benzamide compound, and the molar ratio of cyclodextrine(s), to benzamide compound(s) is no more than 2/1 and no less than 0.1/1.

further comprising an additional active material characterized in that the active material is a herbicide, of nonbenzamide nature selected from the group consisting of triazines, triazoles, diazines, toluidines, urea derivatives, sulphonylureas, benzonitriles, amides, benzoic derivatives, phtalic derivatives, picolinic derivatives, phenolic derivatives and carbamates, including products known under the names: Diuron, Metabenzthiazuron, Isoproturon, Linuron, Chlortoluron, Ametryn, Simizine, Trifluralin, Terbutryn, Propyzamide, Oxadiazon, Napropamide, Metazachlor, Alachlor and Prosulfocarb.

10. Plant protection composition, useful for protecting plants against undesirable plant species, comprising at least one benzamide compound in combination with at least one cyclodextrin so as to improve the mobility of the benzamide compound in the soil, to increase the biological effectiveness of the benzamide compound or to improve both the mobility and increase the biological effectiveness of the benzamide compound, and the molar ratio of cyclodextrine(s), to benzamide compound(s) is no more than 2/1 and no less than 0.1/1.

characterized in that it additionally contains at least one adjuvant selected from the group consisting of vehicles, diluting agents, solvents, disbursing agents, surfactants, emulsifying agents, anti-freezes and dyes, and/or at least one active material selected from the group consisting of herbicides of non-benzamide nature, fungicides, insecticides, nematocides, and bactericides;

and further comprising an additional active material characterized in that the active material is a herbicide, of nonbenzamide nature selected from the group consisting of triazines, triazoles, diazines, toluidines, urea derivatives, sulphonylureas, benzonitriles, amides, benzoic derivatives, phtalic derivatives, picolinic derivatives, phenolic derivatives and carbamates, including products known under the names: Diuron, Metabenzthiazuron, Isoproturon, Linuron, Chlortoluron, Ametryn, Simizine, Trifluralin, Terbutryn, Propyzamide, Oxadiazon, Napropamide, Metazachlor, Alachlor and Prosulfocarb;

said plant protection composition further comprising xanthan gum.

11. Plant protection composition, useful for protecting plants against undesirable plant species, comprising at least one benzamide compound in combination with at least one cyclodextrin so as to improve the mobility of the benzamide compound in the soil, to increase the biological effectiveness of the benzamide compound or to improve both the mobility and increase the biological effectiveness of the benzamide compound, and the molar ratio of cyclodextrine(s), to benzamide compound(s) is no more than 2/1 and no less than 0.1/1;

characterized in that it contains less than approximately 125 g/l of benzamide compound(s).

12. Process for plant protection treatment, for the purposes of protecting both pre- and post-emergence plants against undesirable plant species, comprising the steps of:

preparing a plant protection composition comprising at least one benzamide compound in combination with at least one cyclodextrin whereby the molar ratio of cyclodextrin to benzamide compound is no more than 2/1 and no less than 0.1/1, applying said composition to at least one of the surface and inside the substrate for said plants.

13. Process for plant protection treatment according to claim 12, characterized in that the plants to be protected are selected from the group consisting of cereals, fodders, vegetables, fruits, vines and ornamental trees, shrubs, flowers, and turf.

14. Process for plant protection treatment according to claim 12, characterised in that all or part of the undesirable plant species are dicotyledons, including the chenopiodiaceae, amaranthaceae, cruciferae and solanaceae families.

15. Process for plant protection treatment according to claim 12 characterised in that a composition containing beta-cyclodextrin and Isoxaben is used in preemergence of the plants to be protected.

16. Plant protection composition according to claim 7, characterised in that the cyclodextrin consists essentially of hydroxylated beta-cyclodextrin.

17. Plant protection composition according to claim 11, characterised in that it contains less than approximately from 5 to 120 g/l of benzamide compound(s).

18. Process for plant protection treatment according to claim 13, characterised in that the cereals are selected from the group consisting of maize and winter cereals, and the ornamental trees are conifers.

* * * * *

UNITED STATES PATENT AND TRADEMARK OFFICE
CERTIFICATE OF CORRECTION

PATENT NO. : 6,037,311
DATED : 3-14-2000
INVENTOR(S) : Gosset et al.

It is certified that error appears in the above-identified patent and that said Letters Patent is hereby corrected as shown below:

In column 14, line 29, delete "characterised in that" and insert -- characterized in that --.

In column 14, line 34, delete "characterised in that" and insert -- characterized in that --.

In column 14, line 38, delete "characterised in that" and insert -- characterized in that --.

In column 14, line 41, delete "characterised in that" and insert -- characterized in that --.

In column 14, line 44, delete "characterised in that" and insert -- characterized in that --.

Signed and Sealed this

Tenth Day of April, 2001

Attest:

NICHOLAS P. GODICI

*Attesting Officer*  *Acting Director of the United States Patent and Trademark Office*